(12) United States Patent
Cunniffe et al.

(10) Patent No.: US 8,156,942 B2
(45) Date of Patent: Apr. 17, 2012

(54) METHOD OF IMPLANTING A TRANSMYOCARDIAL STENT

(75) Inventors: Brendan Cunniffe, Galway (IE); Niall Duffy, Galway (IE); Noel Coyle, Galway (IE); Richard William Alan Francis, Minneapolis, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 308 days.

(21) Appl. No.: 12/636,914

(22) Filed: Dec. 14, 2009

(65) Prior Publication Data

US 2010/0094397 A1    Apr. 15, 2010

Related U.S. Application Data

(63) Continuation of application No. 10/887,548, filed on Jul. 7, 2004, now abandoned.

(30) Foreign Application Priority Data

Jul. 22, 2003   (IE) .................................. S2003/0539

(51) Int. Cl.
  *A61B 19/00*   (2006.01)
  *A61F 2/06*    (2006.01)
  *A61M 5/00*    (2006.01)
(52) U.S. Cl. ............................ 128/898; 623/1.11; 604/8
(58) Field of Classification Search ................. 623/1.11, 623/1.12, 1.13, 1.15, 1.35, 1.37; 606/108, 606/153, 155; 128/898; 604/8, 175
See application file for complete search history.

(56) References Cited

U.S. PATENT DOCUMENTS

| | | | |
|---|---|---|---|
| 4,290,427 A | | 9/1981 | Chin |
| 5,275,622 A | | 1/1994 | Lazarus et al. |
| 5,287,861 A | | 2/1994 | Wilk |
| 5,409,019 A | | 4/1995 | Wilk |
| 5,575,685 A | | 11/1996 | Ittah et al. |
| 5,755,682 A | | 5/1998 | Knudson et al. |
| 5,810,849 A | * | 9/1998 | Kontos .......................... 606/144 |
| 5,824,071 A | | 10/1998 | Nelson et al. |
| 5,830,222 A | | 11/1998 | Makower |
| 5,855,577 A | * | 1/1999 | Murphy-Chutorian et al. .. 606/7 |
| 5,855,585 A | * | 1/1999 | Kontos .......................... 606/144 |
| 5,876,411 A | * | 3/1999 | Kontos .......................... 606/144 |
| 5,908,029 A | | 6/1999 | Knudson et al. |
| 5,944,019 A | | 8/1999 | Knudson et al. |
| 5,980,539 A | | 11/1999 | Kontos |
| 5,984,956 A | | 11/1999 | Tweden et al. |
| 5,997,555 A | * | 12/1999 | Kontos .......................... 606/148 |
| 6,001,109 A | * | 12/1999 | Kontos .......................... 606/148 |
| 6,026,814 A | | 2/2000 | LaFontaine et al. |
| 6,029,672 A | | 2/2000 | Vanney et al. |
| 6,035,856 A | | 3/2000 | LaFontaine et al. |
| 6,036,699 A | * | 3/2000 | Andreas et al. ............... 606/139 |
| 6,053,942 A | | 4/2000 | Eno et al. |

(Continued)

FOREIGN PATENT DOCUMENTS

EP    0876803    4/1998

(Continued)

*Primary Examiner* — Darwin Erezo
*Assistant Examiner* — Jing Ou (57) ABSTRACT

According to an aspect of the invention there is provided a method and apparatus for delivering a medical stent to a treatment site for forming a conduit between a blood vessel and a heart chamber. The apparatus comprises a hollow cylindrical body having a proximal end and a distal end, the stent being positioned within the body; and an actuator for expelling the stent from the body to form the conduit.

20 Claims, 3 Drawing Sheets

U.S. PATENT DOCUMENTS

| | | | |
|---|---|---|---|
| 6,068,638 A | 5/2000 | Makower | |
| 6,076,529 A | 6/2000 | Vanney et al. | |
| 6,077,276 A * | 6/2000 | Kontos | 606/144 |
| 6,077,279 A * | 6/2000 | Kontos | 606/148 |
| 6,092,526 A | 7/2000 | LaFontaine et al. | |
| 6,093,166 A | 7/2000 | Knudson et al. | |
| 6,099,542 A | 8/2000 | Cohn et al. | |
| 6,102,941 A | 8/2000 | Tweden et al. | |
| 6,113,630 A | 9/2000 | Vanney et al. | |
| 6,113,823 A | 9/2000 | Eno | |
| 6,123,682 A | 9/2000 | Knudson et al. | |
| 6,126,654 A | 10/2000 | Giba et al. | |
| 6,139,541 A | 10/2000 | Vanney et al. | |
| 6,139,556 A * | 10/2000 | Kontos | 606/144 |
| 6,182,668 B1 | 2/2001 | Tweden et al. | |
| 6,193,726 B1 | 2/2001 | Vanney | |
| 6,196,230 B1 | 3/2001 | Hall et al. | |
| 6,197,050 B1 | 3/2001 | Eno et al. | |
| 6,203,556 B1 | 3/2001 | Evans et al. | |
| 6,214,041 B1 | 4/2001 | Tweden et al. | |
| 6,223,752 B1 | 5/2001 | Vanney et al. | |
| 6,237,607 B1 | 5/2001 | Vanney et al. | |
| 6,250,305 B1 | 6/2001 | Tweden | |
| 6,261,316 B1 | 7/2001 | Shaolian et al. | |
| 6,406,488 B1 | 6/2002 | Tweden et al. | |
| 6,406,491 B1 | 6/2002 | Vanney | |
| 6,409,697 B2 | 6/2002 | Eno et al. | |
| 6,428,549 B1 * | 8/2002 | Kontos | 606/144 |
| 6,451,031 B1 * | 9/2002 | Kontos | 606/144 |
| 6,454,760 B2 | 9/2002 | Vanney | |
| 6,530,914 B1 | 3/2003 | Mickley | |
| 6,554,794 B1 | 4/2003 | Mueller et al. | |
| 6,655,386 B1 | 12/2003 | Makower et al. | |
| 7,179,266 B2 * | 2/2007 | Kontos | 606/144 |
| 2001/0008969 A1 | 7/2001 | Evans et al. | |
| 2001/0012948 A1 * | 8/2001 | Vanney | 606/191 |
| 2001/0044647 A1 | 11/2001 | Pinchuk et al. | |
| 2002/0032478 A1 | 3/2002 | Boekstegers et al. | |
| 2003/0055371 A1 | 3/2003 | Wolf et al. | |
| 2003/0073973 A1 * | 4/2003 | Evans et al. | 604/502 |
| 2003/0078465 A1 | 4/2003 | Pai et al. | |
| 2003/0120195 A1 * | 6/2003 | Milo et al. | 604/19 |
| 2003/0120259 A1 | 6/2003 | Mickley | |
| 2003/0158573 A1 | 8/2003 | Gittings et al. | |
| 2003/0195495 A1 | 10/2003 | Ryan et al. | |
| 2003/0216801 A1 * | 11/2003 | Tweden et al. | 623/1.13 |
| 2004/0064092 A1 * | 4/2004 | Tsugita et al. | 604/101.04 |
| 2004/0077987 A1 * | 4/2004 | Rapacki et al. | 604/8 |
| 2004/0077988 A1 * | 4/2004 | Tweden et al. | 604/8 |
| 2004/0122347 A1 * | 6/2004 | Knudson et al. | 604/8 |
| 2004/0138531 A1 * | 7/2004 | Bonner et al. | 600/156 |
| 2004/0147869 A1 * | 7/2004 | Wolf et al. | 604/8 |
| 2004/0167444 A1 * | 8/2004 | Laroya et al. | 600/585 |
| 2004/0210251 A1 * | 10/2004 | Kontos | 606/224 |
| 2005/0004505 A1 * | 1/2005 | Phelps et al. | 604/8 |

FOREIGN PATENT DOCUMENTS

| | | |
|---|---|---|
| WO | WO98/08456 | 3/1998 |
| WO | WO99/40868 | 2/1999 |
| WO | WO00/21436 | 10/1999 |
| WO | WO00/21461 | 10/1999 |
| WO | WO00/21463 | 10/1999 |
| WO | WO00/41632 | 1/2000 |
| WO | WO00/41633 | 1/2000 |
| WO | WO00/15147 | 3/2000 |
| WO | WO00/15148 | 3/2000 |
| WO | WO/0015149 | 3/2000 |
| WO | WO00/66007 | 5/2000 |
| WO | WO00/66009 | 5/2000 |
| WO | WO01/17440 | 9/2000 |
| WO | WO01/10341 | 2/2001 |
| WO | WO01/10347 | 2/2001 |
| WO | WO01/10348 | 2/2001 |
| WO | WO01/10349 | 2/2001 |
| WO | WO01/17456 | 3/2001 |

* cited by examiner

METHOD OF IMPLANTING A TRANSMYOCARDIAL STENT

CROSS-REFERENCE TO RELATED APPLICATIONS

The present application is a continuation application of U.S. patent application Ser. No. 10/887,548, filed Jul. 7, 2004.

FIELD OF THE INVENTION

The present invention relates generally to a method of using a transmyocardial stent delivery system to deliver a transmyocardial stent.

BACKGROUND OF THE INVENTION

Heart disease is caused by a build-up of cholesterol fats and/or atherosclerotic plaque and/or atherosclerotic lesions within coronary arteries. Over time these lesions grow, progressively narrowing the arteries, thereby restricting the quantity of blood flowing through the artery. Atherosclerosis can lead to myocardial infarction, angina pectoris and/or possibly also be a contributing factor inducing strokes. Heart disease is one of the leading causes of death throughout the world. Those who survive the consequences of heart disease generally experience prolonged suffering and possibly also disability.

Percutaneous transluminal coronary angioplasty (PTCA) is a technique used to clear occluded coronary arteries. Generally a stent is permanently placed within a vessel to hold the lumen open after PTCA, thus reinforcing the vessel wall and improving blood flow. Typically, a stent is a cylindrical shaped device formed from metal or polymers. One form of stent is radially compressed to a diameter that is smaller than that of the vessel in which it is to be deployed to enable it to be delivered to the treatment site. Once the stent has been delivered to the treatment site, it is expanded radially to allow it to contact and support the vessel wall. This type of stent can be crimped onto an expansion device such as a balloon catheter for delivery. Other stent types are fabricated elastically to resist compression in a free state and are releasably compressed for delivery. Both types of stent are expanded radially at the treatment site. Problems can arise if the stent does not fully expand, as the position of the stent may promote the formation of undesirable thrombi. Balloon angioplasty is a procedure in which PTCA is performed and a stent is deployed at the treatment site using a balloon catheter.

Typically, introduction of a stent that elastically resists compression involves introduction of a guidewire percutaneously. The guidewire is then steered to the treatment site through the vascular system. The stent is provided on the distal end of a catheter, which is advanced over the guidewire to the treatment site. The stent is deployed at this site, providing support to a damaged and/or collapsed vessel wall. The radially expandable stent is introduced in a similar manner, however the stent is crimped onto a balloon positioned at the distal end of the catheter and deployment of the stent at the treatment site is effected by inflation of the balloon. A similarly introduced stent could also be used to repair a dissection of a vessel or an aneurysm. Other problems may arise, if gradually over time the stent moves from its original position at the treatment site leaving a weak and vulnerable area of the vessel exposed.

Worldwide figures estimate that approximately 110 million people suffer from diabetes. Recent projections suggest that this figure will have doubled in 10 years. One of the consequences of diabetes is that the blood vessel walls are thinner, consequently the vessels are weaker. Studies have indicated that diabetic patients are more likely to suffer follow-on post balloon angioplasty complications with a five-year mortality rate of approximately 35%. Conversely diabetic patients who have undergone bypass surgery have a five-year mortality rate of 19%. However bypass surgery typically involves considerable trauma, pain and long periods of convalescence.

It is desirable to combine the advantage of coronary artery bypass surgery with the minimally invasive angioplasty/stent delivery technique.

Typically coronary artery bypass graft surgery requires open-chest surgery, which involves an eight to ten-inch incision made in the chest, a thoracotomy. A variety of minimally invasive cardiac surgical techniques have been developed such as the da Vinci technique, which involves robotically assisted surgery requiring only three pencil-sized holes made between the ribs. Through these holes, two robotic-arms and an endoscope (a tiny camera) gain access to the heart, making surgery possible without opening the chest. Coronary artery bypass graft surgery (CABG) is the most commonly performed "open heart" operation. There are approximately 375,000 CABG surgeries performed in the United States each year. Studies show that patients who have minimally invasive operations are released from hospital one to two days earlier than patients recovering from conventional cardiac surgery. Other advantages of minimally invasive surgery can include quicker patient recovery times, less pain, and significantly less scarring than traditional open-heart operations.

However, adoption of new techniques such as the da Vinci technique is typically slow as the specific skill requirements are difficult to acquire and the techniques are more difficult to perform than the traditional by-pass surgery. Many of the new techniques involve direct vascularisation from the ventricle of the heart.

Numerous devices and delivery systems that facilitate these new techniques are disclosed in the prior art.

U.S. Pat. No. 6,113,630 discloses an L-shaped transmyocardial implant, one leg of the L-shaped implant inserts into the coronary artery whilst the other leg inserts into the left ventricle of the heart through the myocardium. The portion of the implant that is positioned in the myocardium has a fabric cuff encircling the exterior surface that is used to integrate the implant with the myocardium and help prevent migration of the implant.

WO 00/15148 discloses a transmyocardial stent that provides a bypass around an occlusion in a coronary artery. The conduit has a section of a blood vessel attached to its interior lumen. Preferably, the section of blood vessel includes at least one naturally occurring one-way valve to prevent the backflow of blood from the coronary artery into the heart chamber.

WO 01/10348 discloses a method and apparatus relating to a conduit placed in the heart wall between the left ventricle and the coronary artery.

WO 00/21461 discloses devices and methods for delivering conduits into the wall of a patient's heart to communicate a coronary vessel with a heart chamber. The device includes a conduit support member which may be in the form of a shaft having a step which defines a recessed portion that receives the conduit. The conduit is covered by a sheath to protect tissue and/or the conduit during its delivery into the heart wall. The sheath is preferably tapered to aid in dilating the opening in the heart wall. The device preferably includes a dilator having a sharpened end and an enlarged end configured to be grasped to manipulate the dilator. There is also an actuator for allowing the sheath to be selectively moved to expose the conduit. The actuator includes a spring for biasing the sheath in a proximal direction.

BRIEF SUMMARY OF THE INVENTION

The present invention seeks to provide an improved stent delivery system and methods of using such a system.

Accordingly, in a first aspect, the present invention provides a medical stent delivery device for delivering a stent to a treatment site, so that the stent forms a conduit between an occluded blood vessel and a heart chamber, the delivery system comprising a hollow cylindrical body having a proximal end and a distal end, stent receiving means positioned at the distal end within the hollow cylindrical body, and actuator means operable for expelling a stent from the stent delivery device in use.

Ideally, the actuator means comprises a plunger mechanism where the stent is expelled from within the hollow cylindrical tube by compression of the plunger mechanism. Alternatively, the actuator means comprises a push-pull wire. A 'flat' profile push-pull wire or such like may be used to push the stent into the desired position and the wire may be of an 'U' profile to sit at the internal wall of the tube and provide maximum force transmission within the restricted tube bore. The push-pull wire may be made from a spring steel or similar material e.g. Nitinol.

A conical or bullet shaped tip (obturator) provided on the distal tip of the profiled push-pull wire is of a suitable profile such that it promotes progression of the stent through the myocardium while also permitting perforation of the posterior wall of the coronary artery, causing no damage to the anterior artery wall.

The stent is radially expandable to form a sealed conduit between the heart and the vessel. The hollow, substantially cylindrical body of the stent delivery system may have any suitable configuration, including in a first embodiment, a straight configuration and in a second embodiment, a curved configuration which is preferably a generally S-shaped configuration.

Advantageously, in the first embodiment with the medical stent delivery system having a straight configuration, the distal end of the hollow cylindrical body of the medical stent delivery system has a puncture means, optionally comprising a puncture needle. Ideally, the medical stent delivery device is used to gain access to the treatment site via a minimally invasive incision made through the patient's chest wall close to the treatment site. An introducer may be employed to provide access to the thoracic area for the delivery system and for other instruments, such as an endoscope. The puncture needle may be manufactured from stainless steel such as 316L or from a stiff thin walled high modulus plastic e.g. LCP.

Ideally the distal end of the medical stent delivery system is advanced through the wall of the heart, the myocardium, to provide access to a heart chamber to obtain a supply of oxygenated blood. Use of a pressure-sensing device will indicate when the distal end of the medical stent delivery system has advanced sufficiently through the wall of the vessel into the chamber of the heart. Ideally the stent is deployed in the myocardium using the actuator means with the distal end of the stent extending through to the heart chamber and the proximal end of the stent projecting out of the myocardial wall to the exterior of the heart. The proximal end of the stent is prevented from radially expanding by use of a sheath mechanism to hold the stent in a radially compressed state. Next an incision is made in the occluded vessel distal to the occlusion and the proximal end of the stent is inserted into this incision, thus forming a conduit between the heart chamber and the occluded vessel to allow oxygenated blood to flow into the vessel by-passing the occlusion. Once the stent is in position the incision in the vessel is repaired using conventional techniques such as a suture or fibrin plug.

Advantageously, in the second embodiment in which the medical stent delivery system has a curved configuration, preferably a generally S-shaped configuration, the medical stent delivery system gains access to the treatment site via a minimally invasive type incision close to the treatment site. It is preferable for another instrument to form this incision Ideally an incision is made through the myocardium using a first puncture device positioned at the distal end of the hollow cylindrical chamber of the medical stent delivery device. Advantageously, a pressure-sensing device is used to indicate when the distal end of the medical stent delivery system has advanced sufficiently through the wall of the vessel into the chamber of the vessel.

The distal end of the medical stent delivery system is advanced through the myocardium into the heart chamber. Ideally the stent is deployed using actuation means through an orifice provided in the S-shaped hollow cylindrical body, preferably on an arcuate section (elbow) of the hollow body.

Advantageously, the stent is prevented from expanding radially by use of a retaining sheath. In the second embodiment in which the delivery device has a generally S-shaped configuration, the proximal end of the stent includes a puncture device. This puncture device makes an incision through the myocardium and then into the diseased, occluded vessel, ideally distal to the occlusion. Once it is established that the stent is in the correct position, the sheath is removed thereby enabling the stent to expand radially thus forming a conduit between the occluded vessel and the heart chamber (preferably, the left ventricle). The S-shaped device is also suitable to operate in this manner even if the diseased, occluded vessel is temporarily shifted to one side in an operating technique which may be employed by a surgeon.

The function of the generally S-shaped-shaped puncture needle device and integral stent delivery system of the present invention is to deploy a stent through the posterior coronary artery wall and the myocardium into a chamber of the heart. With the exception of the location where the stent perforates the posterior coronary artery wall, the generally S-shaped puncture needle device and integral stent delivery system cause minimal trauma to the artery and no dissection or perforation of the anterior artery wall i.e. that wall interfacing with the pericardium. The device is minimally invasive and applicable predominantly to bypassing occlusions of the left anterior descending artery (LAD) or the right coronary artery on the beating heart via a parasternal or left anterior small thoracotomy. Insertion tools, stabilisers and thorascopic devices are required to carry out the procedure and visualisation may be conventional or video-assisted.

Multiple polypropylene stay sutures may be placed on both edges of the fatty epicardium, and these epicardial stay sutures are fixed to immobilise the area in which the puncture needle is to be inserted. A wide angled endoscope is employed to position the puncture needle distal of the occlusion and in the correct position longitudinally relative to the coronary artery. An automated or manual mechanism may be used to promote the puncture needle through the myocardium, and a pressure detector may be used to indicate that depth at which the myocardium is breached as the needle enters the left ventricle. The position of the puncture needle and coronary artery relative to one another and the proposed path for the deployment of the stent are then checked.

Assuming the position of the puncture needle and the aperture for deployment of the stent are correct, an automated or manual mechanism operates the 'flat' profile 'U' push-pull wire to deploy the stent in the desired position. The generally S-shaped puncture device and integral stent delivery system of the invention may incorporate an obturator and/or a tip possessing profile or features that minimise dissection. It is assumed that puncture from a needle is more likely to self-seal than a channel since upon withdrawal of the needle the cells will relax and a haemostatic plug will form.

The puncture needle is designed so that it is capable of deploying a stent through the thickness of an adult heart, assuming the myocardium thickness is 10-15 mm. The puncture needle, regardless of the material of which it is constructed, is radio-opaque or possesses obvious radio-opaque markers. It may be coated with a lubricious coating e.g. hydro-gel or Parylene™ poly(p-xylylene) polymers. The stent may be manufactured from nitinol or a similar material to offer resistance to the pressure of the beating heart that might otherwise plastically deform less resistant materials and to obviate the need for balloon deployment.

In the embodiment of the delivery device having the generally S-shaped configuration, the stent is deployed through an orifice (aperture) in the distal shoulder of the sigmoidal puncture needle. The stent delivery system of the invention employs a removable sheath over the stent to prevent premature expansion and to maintain a low profile prior to deployment. Percutaneous transluminal delivery of contrast media may be necessary to indicate the exact position of the artery.

Advantageously the puncture needle positioned at the distal end of the stent delivery system is designed so that it does not core tissue; instead the puncture needle has a natural inclination to push the muscle fibres apart enabling a clear incision to be formed. The puncture needle is designed so that it is capable of deploying a stent through the thickness of an adult heart, assuming the myocardium thickness is 10-15 mm. Generally, the myocardium thickness is 10-15 mm for healthy adults; however, it could be thinner and possibly thicker for some conditions.

In a preferred arrangement, the puncture needle is formed from stainless steel or a stiff thin walled high modulus plastic such as LCP. Ideally the puncture needle also contains radio-opaque markers. It is preferable for the puncture needle to be coated with a lubricous coating.

A "flat" profile push-pull wire may be used to manipulate the stent into position in the stent delivery system in both configurations. Ideally this wire is made from a spring steel or similar material for example Nitinol.

The present invention further provides a sheath mechanism which wraps around the stent while in a compressed position in the medical stent delivery system. Preferably the sheath mechanism prevents the stent from expanding. Advantageously the sheath mechanism is removed by unwinding when so desired allowing the stent to radially expand.

According to another aspect, the present invention further provides a plurality of stent types, the profile of which incorporates anchoring means for anchoring the stent firmly in position, when deployed for use. These stent types are suitable for use with the present medical stent delivery devices.

Advantageously, each of the plurality of stent types provided for use with the stent delivery system has a different configuration, each configuration providing enhanced anchoring properties to prevent migration of the stent when in position at the treatment site. The stent types of the invention may comprise a hollow cylindrical body made with a plurality of interconnected rings, wherein the rings extend circumferentially around the hollow cylindrical body and the rings are connected by a series of link elements.

In a first embodiment, the stent has a cylindrical body with flared ends or flanged ends. Ideally the flared or flanged ends provide a means for anchoring the stent in position in the vessel. It is preferable for the flared ends or flanged ends to be formed integrally with the stent.

A second embodiment of the stent has a cylindrical body, wherein the diameter of a first end of the stent is substantially larger than that of a second end and the diameter of the body of the stent decreases gradually from that of the first end to that of the second end in a tapering effect. Therefore there is a gradual decrease in diameter of each interconnected ring from the widest at the first end to the narrowest at the second end over the body of the stent.

Alternatively, the stent may also have a cylindrical body, wherein the diameter of the first end of the stent is substantially larger than that of the second end and the body of the stent comprises two connected portions. Ideally the diameters of the interconnected rings of a first portion gradually decrease from the widest diameter at the first end of the stent to the narrowest diameter which is equivalent to the diameter of the second end of the stent. Ideally the diameter of the second portion has a constant diameter which is the diameter of the second end of the stent. Advantageously the two portions are fused together. Ideally the fusion point of the two portions is at the point where the diameters are equivalent to that of the narrowest second end diameter. Optionally the first and second portion may be formed integrally with one another.

It is preferable for the degree of reduction in the diameter of the interconnected rings in either of the second embodiments of the stent to be determined with regard to the diameter of the first and second ends and the distance between the largest diameter interconnected ring and the narrowest diameter interconnected ring of the stent. Advantageously the taper effect provides means for the stent to resist migration from the original treatment site in the vessel over a period of time.

A third embodiment of the stent has a generally cylindrical body, wherein the diameter of opposed first end and second end of the stent are equivalent in size and the diameter of the central section of the body of the stent is narrower than that of the first and second ends of the stent. Advantageously, the stent includes anchoring means that help prevent stent migration when in position at the treatment site.

In a fourth embodiment, the stent comprises a first and second portion, wherein the first portion comprises a cylindrical body and the second portion comprises a curved hollow tubular section. Advantageously both portions have the same diameter. Ideally the curved hollow tubular section curves about an angle of 90°. Advantageously the angle of curvature is not limited to 90°, and any suitable angle of curvature can be used. It is preferable for the first and second portions to be formed integrally with each other. Advantageously the first and second portions can also be fused together.

Yet a further, fifth embodiment of the stent has an opening in the cylindrical body of the stent. It is preferable for the opening to be positioned in the body of the stent at either end of the stent. Advantageously the end at which the opening is positioned is sealed to provide extra protection for the treatment site. Ideally, the stent directs the flow of blood when in position at the treatment site.

In a sixth embodiment, the stent comprises two hollow cylindrical end sections connected with a flexible mid-section. Ideally the mid-section of the stent comprises a ring or a plurality of rings and/or interlinking members which extend circumferentially around the diameter of the hollow cylindrical ends in a helical arrangement. This allows for variation in the thickness of the vessel when the stent is in situ.

A seventh embodiment of the stent, the stent comprises two hollow cylindrical end sections connected by a mid-section. Ideally the mid-section comprises a hollow cylindrical body that has been compressed into a bellows arrangement, enabling the mid-section to lengthen and shorten as required as a vessel in which the stent is placed expands and contracts.

Advantageously the plurality of stents described above can be either self-expanding, elastically resisting compression in a free state, or radially expandable where the stent is expanded using an expansion device such as a balloon catheter. Clearly, the sheath mechanism is not necessary if an expansion device is required to expand the stent. Ideally the self-expanding stents are formed from a material which offers resistance to the pressure of a beating heart which pressure might otherwise plastically deform less resistant materials. Such materials include nitinol, nickel free self-expanding alloys or self-expanding polymers. Advantageously the radially expandable stents are formed from stainless steel. The stents are not limited to these materials and any suitable material known to a person skilled in the art can be used. Advantageously, the present invention also provides a plurality of stents comprising a hollow cylindrical body made out of a solid tubular material.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description of the invention is merely exemplary in nature and is not intended to limit the invention or the application and sues of the invention. Furthermore, there is no intention to be bound by any theory presented in the preceding background of the invention or the following detailed description of the invention.

Referring initially to FIGS. 1 to 10, ten embodiments of stents indicated generally by reference numerals 1 to 10, inclusive are shown for use in and deployment from the stent delivery devices of the invention.

Figure 1:
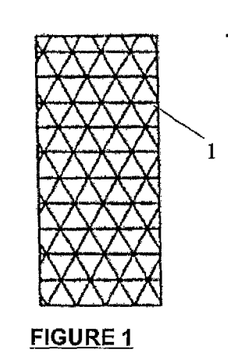
FIGS. 1 to 10 are side views of ten embodiments of stents of the invention.

FIG. 1 shows a cylindrical stent 1 which has the form of a known stent. The design of the stent can be varied appropriately to suit the requirements of its use. Thus, radial strength, provision of wall support, longitudinal/radial flexibility and geometric size can be varied appropriately to suit the requirements of its use. Thus, radial strength, provision wall support, longitudinal/radial flexibility and geometric size can all be varied as required.

Figure 2:
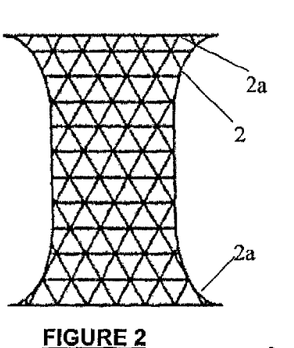
Figure 3:
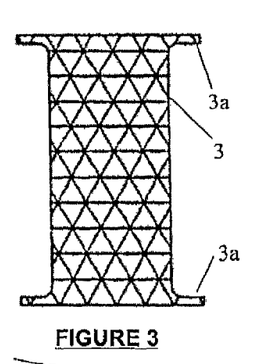

In FIGS. 2 and 3, there are shown two stents 2 and 3 each having a cylindrical body with flared ends 2*a* and with flanges 3*a*, respectively. The flared ends 2*a* have the advantage of assisting in anchoring the stent in position in the myocardium and in the vessel, when in use. Provision of flanges 3*a* on the stent 3 has the benefit of providing an anchoring means for anchoring the stent 3 in the heart while also aiding in attaching the artery to the heart.

Figure 4:
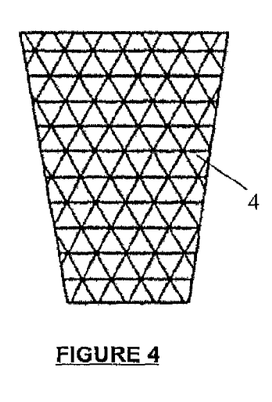

FIG. 4 shows a stent 4 having a tapered body, which has the advantage that stent 4 resists migration of the stent when in use. Since movement of the stent is restricted to some degree by the vessel walls within which it has been placed, the likely direction of migration is in the direction of the left ventricle chamber; consequently the end of the stent/shunt with the wider diameter is placed in the vessel and the end with the narrower diameter placed in the heart. The provision of the tapered walls on stent 4 benefits blood flow dynamics when the stent is in use.

Figure 5:
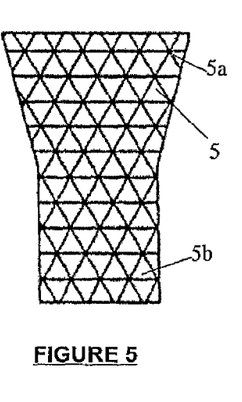

FIG. 5 shows a stent 5, which has a tapered section 5*a*, and a cylindrical section 5*b*. The provision of the tapered section 5*a* on stent 5 allows stent 5 to resist migration in addition to benefiting blood flow dynamics.

Figure 6:
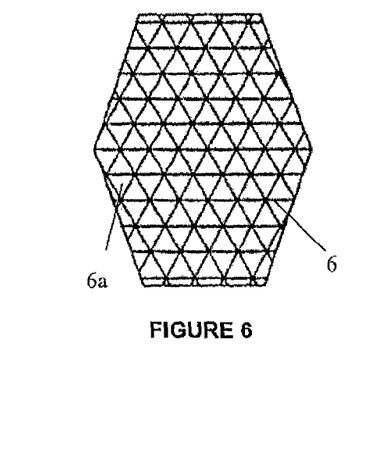

FIG. 6 shows stent 6 having a central section 6*a* which has the largest diameter and a tapered section on both sides of the central section 6*a*. The tapered sections on stent 6 provide anchoring means and also assist in improving blood flow dynamics when the stent 6 is in use.

Figure 7:
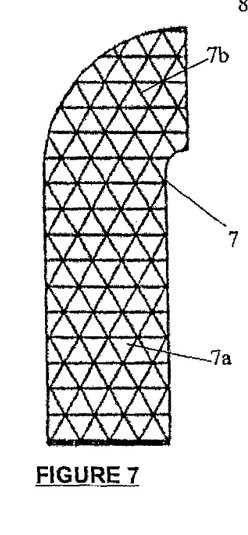

FIG. 7 shows a stent with a cylindrical body 7*a* having a curved tubular section 7*b* for placement inside the artery. The curved section 7*b* of stent 7 is used to direct blood flow from the left ventricle of the heart to the diseased blood vessel (artery) distal of the lesion. The curved section 7*a* has the further advantage that it protects the region of the blood vessel that is punctured when the stent delivery device punctures the blood vessel when delivering the stent. The method of delivery of the stent is described further below.

Figure 8:
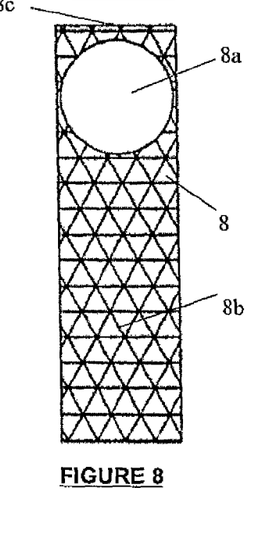

FIG. 8 shows a stent 8 with channel 8*a* in the side wall 8*b* with the channel 8*a* being aligned in the direction of the blood flow to provide a blood flow path. The opposed end 8*c* of the stent 8 is sealed to protect the region of the blood vessel in which the puncture is made when the stent is being deployed by the stent delivery device of the invention.

Figure 9:
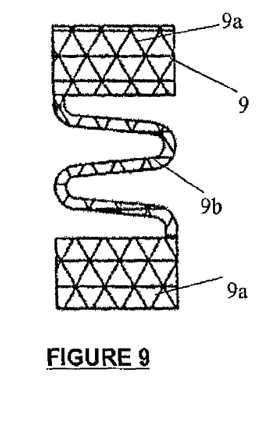

FIG. 9 shows a stent 9, with two cylindrical end sections 9*a* with a flexible mid-section 9*b* to allow for variation in the thickness of the myocardium due to the contraction and relaxation of the beating heart. The flexible mid-section adopts generally helical configuration.

Figure 10:
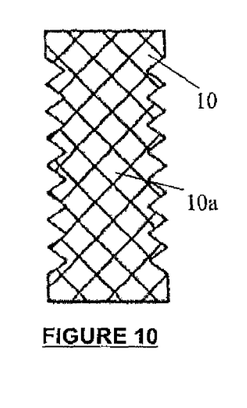

FIG. 10 shows a cylindrical stent 10, with a central portion of the cylindrical body having a "bellows" configuration 10*a*, which configuration enables the stent to expand and contract when in position at the treatment site. Thus the "bellows" configuration provides stent 10 with the same advantage as the flexible mid-section 9*b* provides to stent 9.

Figure 11:
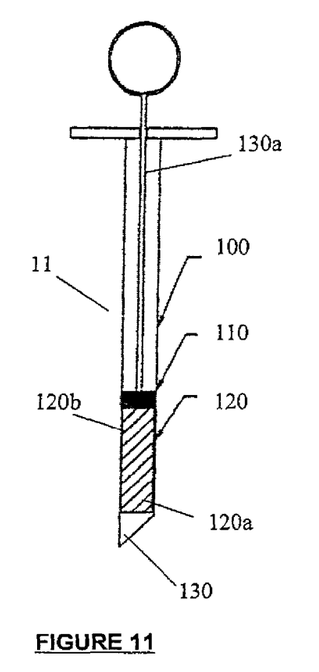
FIG. 11 is a cross-section side view of a first embodiment of a medical stent delivery system of the invention.

Referring now to FIG. 11, a first embodiment of the medical stent delivery system 11 having a linear configuration will be described. The medical stent delivery system 11 comprises a hollow cylindrical body 100 with puncture needle 130, a stent 120 positioned at the distal end within the hollow cylindrical body 100 and an actuator means 110. The actuator means can be a manual plunger mechanism or an automated hydraulic or a linear variable-displacement transducer (LVDT) type device. The actuator means, regardless of its mode of power, is required to actuate the expulsion of the stent. In this embodiment, the actuator 110 comprises a plunger mechanism for expelling the stent from within the hollow cylindrical tube by compression of a plunger 130*a*.

The procedure for using the medical stent delivery system 11 begins with the surgeon gaining access to the target vessel by a small incision in the chest cavity of the patient. An introducer may be used to provide an access port for surgical devices which the surgeon needs to use. This introducer is able to facilitate the surgeon's use of an endoscope with light source, a heart stabilising device such as the Medtronic EndoOctopus™ cardiac stabilizer, as well as the stent delivery device 11 or a puncture tube and various standard surgical tools for use in minimally invasive surgery such as suturing devices, probes, scissors, and stabilisers. The target vessel is then accessed through pericardial sac. Depending on which of the type of stent 1-10 is being used, one of the following surgical techniques denoted A, B, and C is then used.

A. First Possible Surgical Technique for Use with Stent Delivery Device 11: The surgeon locally removes the artery from the surface of the heart and moves it slightly (3-5 mm) to one side. The sheathed puncture needle 130 positioned at the distal end of stent delivery device 11 is now introduced through the incision in the patient's chest wall, optionally through an introducer and into the heart wall until it pierces the wall of the left ventricle. Then the puncture needle 130 is advanced and passes into the left ventricle. A pressure-sensing device may be used to indicate when the puncture needle 130 has advanced into the left ventricle. Alternatively, this will be determined by the surgeon visually by noting blood flow through to the proximal end of the delivery device 11. The stent 120 is deployed into position in the inner myocardial wall using the actuator 110. When deployed, the distal end of the stent 120a is positioned in the inner wall of the myocardium and projects into the left ventricle while the proximal end 120b of the stent protrudes by about 3 mm out from the outer wall of the myocardium. The proximal end 120b of the stent is prevented from expanding radially by use of a sheath mechanism (not shown). The surgeon now makes an incision in the underside of the occluded vessel on the side of the occlusion distal the heart and the surgeon places the proximal end 120b of the stent is inserted into this incision. Thus, a conduit or shunt is formed between the left ventricle and the artery distal of the occlusion, thereby supplying an improved flow of oxygenated blood to the vessel (most likely, this vessel is an artery).

B. Second Possible Technique for Use with Stent Delivery Device 11: In a variation of the technique described above in A, the surgeon proceeds as described in A, except that he uses a device for restricting the proximal end of the stent from expanding until it is positioned in the artery. Use of this restricting device allows for a smaller incision to be made in the artery. The stent may be designed so as to have a proximal end which facilitates this restriction, thereby further enabling the surgeon to require only a smaller incision then otherwise possible.

C. Third Possible Technique for use with Stent Delivery Device 11:
An alternative technique is also possible in which the stent delivery device 11 is advanced through the vessel (artery) without the surgeon having to move the vessel to one side. In this technique, the surgeon proceeds initially to access the target site as set out above in the paragraph preceding the description of the first technique A. Then, instead of moving the artery to the side as in technique A, the surgeon deploys the stent in a controlled manner such that the puncture needle 130 punctures the vessel at the side proximal to the surgeon and then passes through the vessel and through the opposed wall of the artery and then through the myocardium. Thus, there are two incisions at opposed side walls of the artery with this technique. The actuator mechanism 130a is then activated so that the stent is delivered through the artery into the left ventricle with the stent distal end 120a in the left ventricle and the stent proximal end 120b remaining in the artery thereby enabling blood flow from the left ventricle through the stent and into the vessel (artery) at a point distal to the lesion. The incision on the upper side of the vessel (i.e. the side of the vessel proximal to the surgeon) is then closed by a known method e.g. a suture or fibrin plug. By using smaller diameter stents, it is possible to reduce further the outer diameter of the delivery device and this allows for reduction in the size of the puncture wound even more. With a smaller diameter stent, there may be a necessity to place one or more additional stents to obtain sufficient blood flow.

Figure 12:
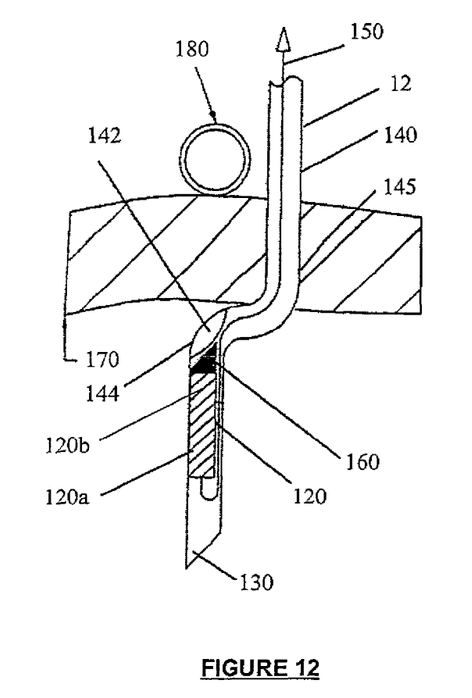
FIG. 12 is a cross-section side view of a second embodiment of a medical stent delivery system of the invention.
Figure 13:
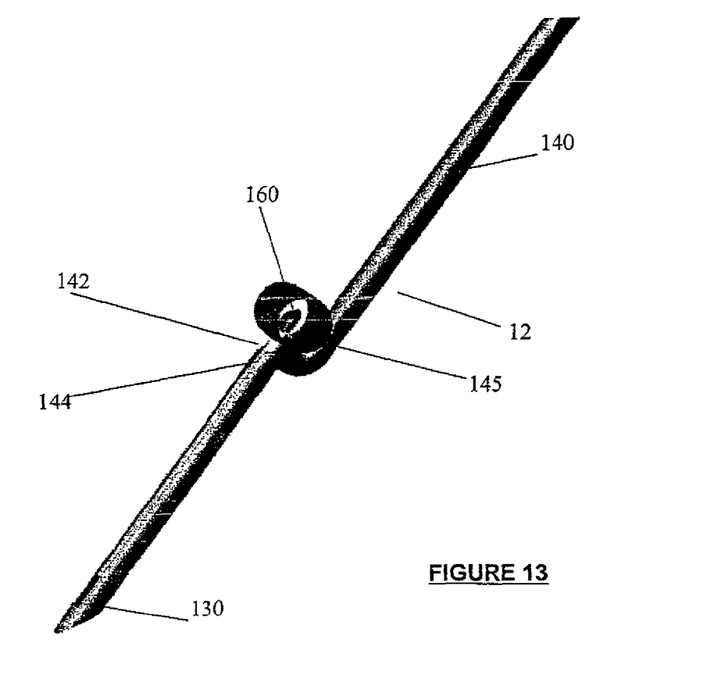
FIG. 13 is a perspective view of a second embodiment of the medical stent delivery system of FIG. 12.

Referring now to FIGS. 12 and 13, a second embodiment of the medical stent delivery device 12 having a curved generally S-shaped configuration will be described. The curved S-shaped delivery system 12 comprises an arcuate hollow cylindrical body 140 which has a generally S-shaped configuration including a first arcuate section (elbow) 144 and a second arcuate section (elbow) 145. The hollow cylindrical body 140 includes a puncture needle 130, a stent 120 positioned at the distal end within the hollow cylindrical body 140 and an actuator means 150 comprising a push-pull wire which is removably engaged with the distal end of the stent 120. There is a second puncture device 160 positioned at the proximal end 120b of the stent 120. The hollow cylindrical body 140 includes an orifice 142 located at an arcuate portion of the hollow cylindrical body i.e. at the "elbow 144" of the hollow cylindrical body located in the region accessible to an occluded vessel 180.

As before, the S-shaped delivery device 12 gains access to the treatment site via a minimally invasive type incision made by a surgeon in the patient's chest, close to the treatment site. Usually another instrument is used to make this incision. In use, the stent delivery device 12 punctures the artery from underneath and thus has the advantage of only one perforation in the artery. There are three possible alternative methods by which the surgeon can use the second embodiment of the delivery device 12, namely techniques D, E, and F described below. Device 12 is used initially in a similar way as the first embodiment of the device 11 in that it is introduced through an introducer via an incision in the patient's chest.

D. First Technique for use with Delivery Device 12:
In the first technique, the device 12 is introduced beside the artery at a point distal to the lesion as shown in FIG. 12 and the puncture device 130 at the distal end of the delivery device 12 makes an incision through the myocardium 170. A pressure-sensing device can be used to indicate when the distal end of the delivery system 12 has advanced sufficiently through the myocardium into the heart chamber. A heart stabilization device such as Medtronic EndoOctopus™ cardiac stabilizer is used to hold the heart surface in the region of the operating site. Once in position, the stent and its retaining sheath are advanced out of the delivery device through the myocardium and into the artery.

The stent 120 is deployed using the pull-push wire 150. Before deployment of this wire, the stent 120 is positioned within the heart to the inner side of the myocardium 170. The stent 120 is prevented from expanding radially by use of a sheath mechanism (not shown). The proximal end 120b of the stent 120 has a puncture device 160 which forms an incision in and through the myocardium on deployment of the wire 150 in the direction of the arrow in FIG. 12. Thus, the stent 120 is drawn through the orifice 142 and through the myocardium and then the wall of the diseased occluded vessel 180. The end of the wire 150 which engages the distal end of the stent 120 has a 'flat' or 'U' profile shape which provides maximum force transmission for moving the stent within the restricted bore of the delivery device 12. The push-pull wire 150 may be made from a spring steel or similar material e.g. TiNi alloy (nitinol). Once it is established that the stent 120 is in the deployed position in the myocardium and the vessel

180, the sheath is removed thereby enabling the stent 120 to radially expand forming a conduit between the heart and the vessel.

As shown in FIG. 12, the generally S-shaped device 12 is pushed down sufficiently into the ventricle until the orifice 142 at the first elbow 144 of the hollow cylindrical body 140, is below the inner wall of the myocardium 170. This allows the puncture device 160 and stent 120 to be pulled upwardly and in through the lumen of the vessel 180 to revascularized.

E. Second Technique for use with Delivery Device 12:

In the second possible method, the vessel is moved to one side by the surgeon and the needle is inserted into the myocardium at the location where the vessel was positioned. This allows for a sharper bend on the S-shaped puncture needle and thus enables a straight travel path for the stent from the myocardium up into the vessel. Once positioned, the vessel is moved back into its original position and the stent and sheath advanced as described previously. Once positioned in the vessel the sheath can be removed and the stent deployed.

Figure 14:
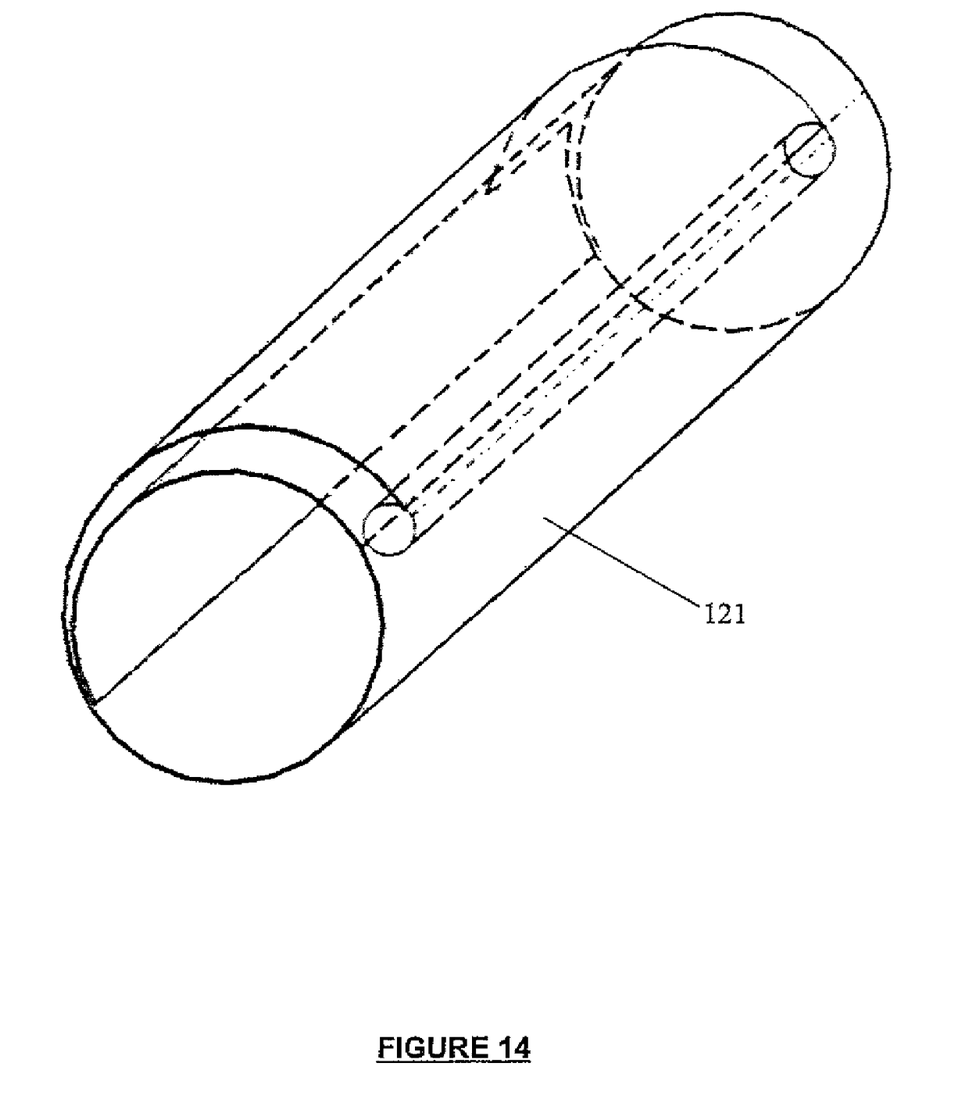
FIG. 14 is a perspective view of a sheath of the medical stent delivery system of the invention.

F. Third Technique for use with Delivery Device 12:

A potential third technique of the S-shaped puncture device 12 utilises the method as described in technique E but the device 12 incorporates a new sheath mechanism 12 which wraps around the stent 120 while in a compressed position in the delivery device 12. The sheath mechanism prevents the stent 120 from expanding until desired. To release the stent, the sheath is unwound off the stent. This requires a slight modification to the puncture needle. FIG. 14 illustrates the modified delivery device with a slit in the distal section of the tube to allow the stent to be deployed therefrom upon retraction/unwinding of the sheath.

A potential problem of retrograde blood flow may arise with the above described devices. Retrograde flow arises where the blood uses the conduit created by the stent as a passage back into the left ventricle. This problem can be overcome by placing a one-way valve in the conduit which only allows blood to flow from the left ventricle to the vessel (artery). Another potential method of overcoming the problem of retrograde flow is to seal off the lesion fully. This could be achieved by placing a mechanical blocking device in the lesion. It may be possible to seal off the lesion by suturing the artery closed distal to the lesion. It may also be possible to place a fibrin block/patch in the lesion to prevent the retrograde blood flow.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims.

What is claimed is:

1. A method for bypassing a lesion in a coronary artery comprising the steps of:
    inserting a delivery device adjacent the coronary artery distal of the lesion through an outside surface of the myocardium of a heart, wherein the delivery device includes a hollow cylindrical body having a proximal end, a distal end, a substantially elbow-shaped curve, and an opening in the body proximate the elbow-shaped curve and between the proximal end and the distal end, wherein the delivery device is inserted into the myocardium such that the distal end is disposed within a chamber of the heart and the opening is disposed inside of the outside surface of the myocardium;
    deploying a stent disposed with the cylindrical body through the opening such that the stent exits the myocardium and enters into the coronary artery distal of the lesion; and
    radially expanding the stent to form a conduit between the chamber and the coronary artery.

2. The method of claim 1, wherein the delivery device includes a first puncture device coupled to the distal end of the cylindrical body.

3. The method of claim 2, further comprising a second puncture device coupled to a proximal portion of the stent such that during the deploying step the second puncture device forms an incision through the myocardium and then through a wall of the coronary artery.

4. The method of claim 1, wherein the step of inserting the delivery device comprises inserting the delivery device such that the opening is inside of an inner wall of the myocardium.

5. The method of claim 1, wherein the cylindrical body is s-shaped.

6. The method of claim 1, wherein the step of deploying the stent comprises utilizing a push-pull wire coupled to the stent.

7. The method of claim 6, wherein the push-pull wire has a flat or U-shaped profile.

8. The method of claim 1, wherein the stent is self-expanding and the step of radially expanding the stent comprises removing a sheath that surrounds the stent.

9. The method of claim 1, wherein prior to inserting the delivery device the coronary artery is moved to a side, wherein the delivery device is inserted into the myocardium at a location of the coronary artery prior to the coronary artery being moved, and wherein after the delivery device is inserted, the coronary artery is moved back to its original position.

10. The method of claim 1, wherein the conduit is formed such that a first end of the stent is disposed in the heart chamber and a second end of the stent is disposed in the coronary artery.

11. A method for forming a conduit between a blood vessel and a heart chamber comprising the steps of:
    inserting a delivery device adjacent the blood vessel through an outside surface of the myocardium of the heart, wherein the delivery device includes a hollow cylindrical body having a proximal end, a distal end, a substantially elbow-shaped curve, and an opening in the body proximate the elbow-shaped curve and between the proximal end and the distal end, wherein the delivery device is inserted into the myocardium such that the distal end is disposed within the heart chamber and the opening is disposed inside of the outside surface of the myocardium;
    deploying a stent disposed with the cylindrical body through the opening such that the stent exits the myocardium and enters into the blood vessel; and
    radially expanding the stent to form the conduit between the heart chamber and the blood vessel.

12. The method of claim 11, wherein the delivery device includes a first puncture device coupled to the distal end of the cylindrical body.

13. The method of claim 12, further comprising a second puncture device coupled to a proximal portion of the stent such that during the deploying step the second puncture device forms an incision through the myocardium and then through a wall of the blood vessel.

14. The method of claim 11, wherein the cylindrical body is s-shaped.

15. The method of claim 11, wherein the step of deploying the stent comprises utilizing a push-pull wire coupled to the stent.

16. The method of claim 15, wherein the push-pull wire as a flat or U-shaped profile.

17. The method of claim 11, wherein the stent is self-expanding and the step of radially expanding the stent comprises removing a sheath that surrounds the stent.

18. The method of claim 11, wherein prior to inserting the delivery device the blood vessel is moved to a side, wherein the delivery device is inserted into the myocardium at a location of the blood vessel prior to the coronary artery being moved, and wherein after the delivery device is inserted, the blood vessel is moved back to its original position.

19. The method of claim 11, wherein the step of inserting the deliver device comprises inserting the delivery device such that the opening is disposed in the heart chamber.

20. The method of claim 11, wherein the conduit is formed such that a first end of the stent is disposed in the heart chamber and a second end of the stent is disposed in the blood vessel.

* * * * *